United States Patent
Das et al.

(10) Patent No.: US 12,420,079 B2
(45) Date of Patent: Sep. 23, 2025

(54) BLOOD PUMP WITH IMPROVED LEAKAGE CONTROL

(71) Applicant: ABIOMED, INC., Danvers, MA (US)

(72) Inventors: Soumen Das, Danvers, MA (US);
Qingchao Kong, Danvers, MA (US);
Zhenghong Tao, Danvers, MA (US);
Alexander Ship, Danvers, MA (US)

(73) Assignee: ABIOMED, INC., Danvers, MA (US)

( * ) Notice: Subject to any disclaimer, the term of this patent is extended or adjusted under 35 U.S.C. 154(b) by 0 days.

(21) Appl. No.: 18/640,108

(22) Filed: Apr. 19, 2024

(65) Prior Publication Data
US 2025/0090832 A1 Mar. 20, 2025

Related U.S. Application Data

(63) Continuation of application No. 17/144,570, filed on Jan. 8, 2021, now abandoned.
(Continued)

(51) Int. Cl.
*A61M 60/411* (2021.01)
*A61M 60/135* (2021.01)
(Continued)

(52) U.S. Cl.
CPC ........ *A61M 60/411* (2021.01); *A61M 60/135* (2021.01); *A61M 60/806* (2021.01);
(Continued)

(58) Field of Classification Search
CPC ............. A61M 60/135; A61M 60/411; A61M 60/806; A61M 60/829; H02K 3/30; H02K 5/02; H02K 15/10; H02K 15/14
See application file for complete search history.

(56) References Cited

U.S. PATENT DOCUMENTS

| | | |
|---|---|---|
| 5,089,016 A | 2/1992 | Millner et al. |
| 5,911,685 A | 6/1999 | Siess et al. |

(Continued)

FOREIGN PATENT DOCUMENTS

| | | | | |
|---|---|---|---|---|
| EP | 3319098 A1 | 5/2018 | | |
| EP | 3542835 A1 * | 9/2019 | ............ | A61M 60/13 |

(Continued)

OTHER PUBLICATIONS

Office Action from Japanese Patent Application No. 2022-542124 dated Dec. 17, 2024 (6 pp.).

(Continued)

*Primary Examiner* — Kenneth J Hansen
(74) *Attorney, Agent, or Firm* — Botos Churchill IP Law LLP

(57) ABSTRACT

A blood pump with a stator and rotor wherein the rotor is assembled by bonding the stator components with epoxy. The bonding surfaces of the rotor components are primed with a silane-based primer to improve adhesion between the primer and the rotor components by rendering such surfaces hydrophobic. A bonding surface of one of the stator yoke or the stator sleeve, or both, is treated with a primer that improves wettability of the bonding surface and improves bonding of the epoxy to the binding surface. The device has a bonding surface adhered to epoxy in which a primer was applied on such bonding surface prior to introducing epoxy onto the bonding surface. In addition to improved bond strength, hydrophobic surface would control moister ingress.

14 Claims, 11 Drawing Sheets

Related U.S. Application Data

(60) Provisional application No. 62/959,552, filed on Jan. 10, 2020.

(51) Int. Cl.
  *A61M 60/806* (2021.01)
  *A61M 60/829* (2021.01)
  *F04D 9/00* (2006.01)
  *F04D 13/06* (2006.01)

(52) U.S. Cl.
  CPC .............. *A61M 60/829* (2021.01); *F04D 9/00* (2013.01); *F04D 13/06* (2013.01); *A61M 2207/00* (2013.01)

(56) References Cited

U.S. PATENT DOCUMENTS

| | | | |
|---|---|---|---|
| 6,245,007 | B1 | 6/2001 | Bedingham et al. |
| 6,794,789 | B2 | 9/2004 | Siess et al. |
| 7,011,620 | B1 | 3/2006 | Siess |
| 9,402,942 | B2 | 8/2016 | Hastie et al. |
| 9,872,948 | B2 | 1/2018 | Siess |
| 2004/0139887 | A1 | 7/2004 | Zhang |
| 2008/0024024 | A1* | 1/2008 | Tamaoka ............. H02K 5/1675 310/90 |
| 2015/0151031 | A1 | 6/2015 | Yaghdjian |
| 2018/0228953 | A1 | 8/2018 | Siess et al. |
| 2018/0280598 | A1 | 10/2018 | Curran et al. |

FOREIGN PATENT DOCUMENTS

| | | |
|---|---|---|
| EP | 3567619 A1 | 11/2019 |
| JP | 2014121222 A * | 6/2014 |
| TW | 434034 B | 5/2001 |

OTHER PUBLICATIONS

Action issued in Chinese Patent Application No. 202180008634X dated Feb. 22, 2025 (8 pp.).

"A Guide to Silane Solutions," Dow Corning Corporation, 2009.

International Search Report and Written Opinion for PCT Application No. PCT/US21/70013 dated Mar. 22, 2021.

Morita etal., Resin Mold Structure Body—"JP2014121222A_MT", (Jun. 2014) (Year: 2014).

Office Action from Israeli Patent Application No. 294353 dated Dec. 23, 2024 (3 pp.).

Office Action and Search Report issued in Chinese Patent Application No. 202180008634.X, mailed Jul. 6, 2024, 16 pages.

Office Action from Taiwan Patent Application No. 110100704 dated May 20, 2024 (30 pp.).

Office Action issued in Chinese Patent Application No. 202180008634X on Jun. 27, 2025 (11 pp.).

Examination Report No. 1 issued in Australian patent application No. 2021205985, dated Aug. 7, 2025 (3 pp.).

* cited by examiner

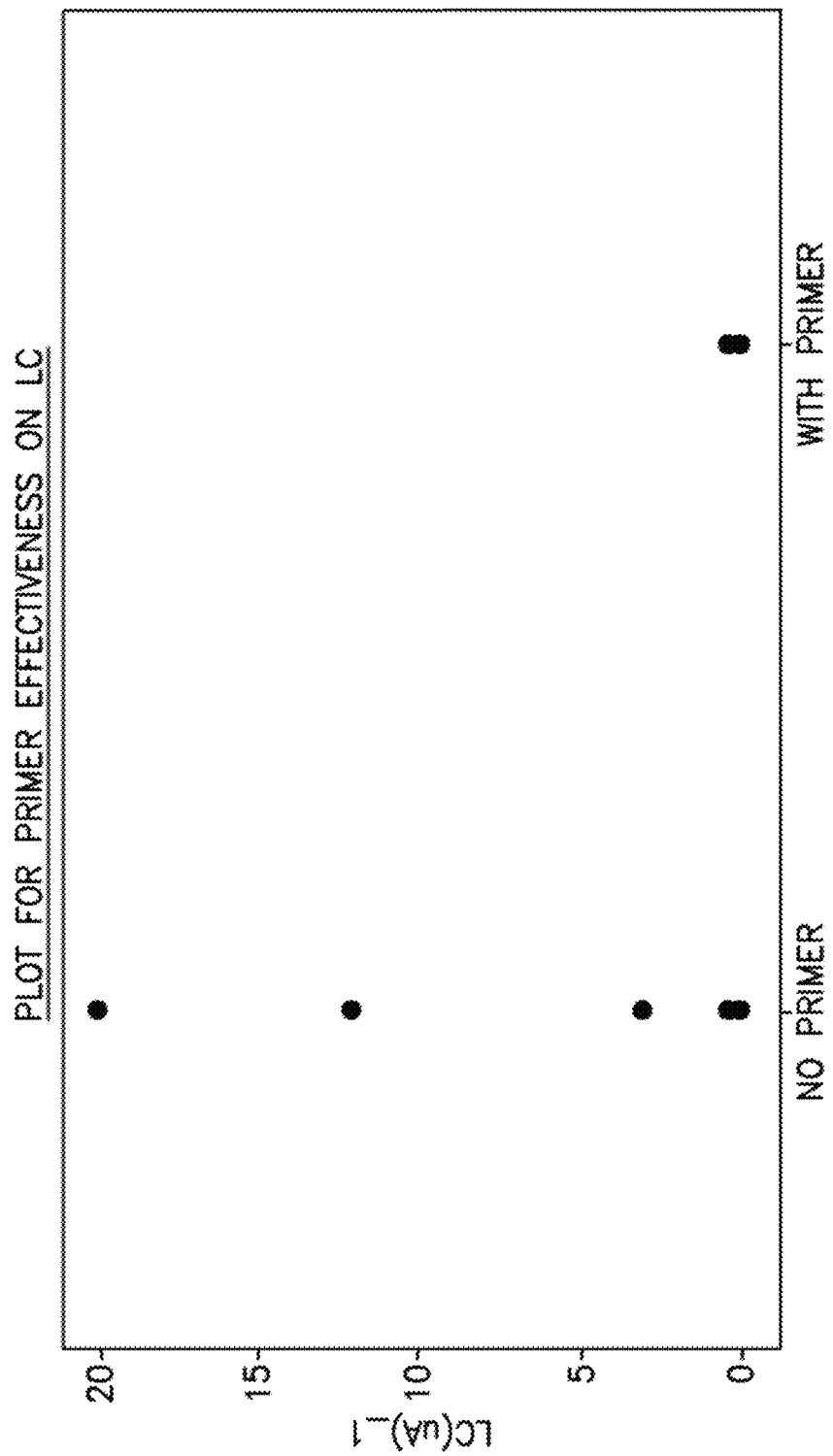

_US 12,420,079 B2_

BLOOD PUMP WITH IMPROVED LEAKAGE CONTROL

CROSS REFERENCE TO RELATED APPLICATION

The present application is a continuation of U.S. application Ser. No. 17/144,570, filed Jan. 8, 2021, now abandoned, which claims the benefit of U.S. Provisional Application No. 62/959,552, filed Jan. 10, 2020, the disclosures of all of which are incorporated by reference herein in their entirety.

TECHNICAL FIELD

This invention relates to a blood pump, in particular an intravascular blood pump, to support a blood flow in a patient's blood vessel.

BACKGROUND

Blood pumps of different types are known, such as axial blood pumps, centrifugal blood pumps, or mixed-type blood pumps, where the blood flow is caused by both axial and radial forces. Intravascular blood pumps are inserted into a patient's vessel such as the aorta by means of a catheter. A blood pump typically comprises a pump casing having a blood flow inlet and a blood flow outlet. In order to cause a blood flow from the blood flow inlet to the blood flow outlet, an impeller or rotor is rotatably supported with the pump casing about an axis of rotation, with the impeller being provided with one or more impeller blades for conveying blood. A blood pump is described in US Patent Publication No. 2018/0228953 to Seiss et al., which is incorporated by reference herein. Pumps are also described in U.S. Pat. No. 5,911,685 entitled "Method and Apparatus for Cardiac Blood Flow Assistance" to Seiss et al., U.S. Pat. No. 6,794,789 entitled "Miniature Motor" to Seiss et al., U.S. Pat. No. 9,402,942 to Hastie et al. entitled "Loading Guide Lumen" and U.S. Pat. No. 9,872,948 to Siess, all of which are incorporated by reference herein.

The motor 100 of a blood pump is illustrated in FIG. 1. The impeller has a drive unit 111 and impeller blades 110 are on the distal end 126 of the motor 100. The motor 100 has a stator 120 and a rotor 130. The skilled person is aware that rotary systems typically have a stator (the stationary portion) and a rotor (the rotating portion). FIG. 2 illustrates the motor of FIG. 1 in an exploded view with the rotor 130 outside the stator 120.

FIG. 3 is an exploded view of the stator. The stator has a yoke 121, a coil 122, and a coil holding sleeve 123. The yoke 121 is typically made of metal, while the coil 122 is typically made of copper. The coil holding sleeve 123 can be either plastic or ceramic. These components are illustrated in an exploded view in FIG. 3. The coil holding sleeve 123 in FIG. 3 is made of ceramic.

FIG. 4 is a cross section of the stator of FIG. 2 and also illustrates the yoke 121, the coil 122 and the coil holding sleeve 123. The stator is assembled using epoxy adhesive 124 to provide a stable and secure assembly. The epoxy 124 essentially encapsulates the coil 122 such that epoxy 124 is at the yoke 121/coil 122 interface and the coil 122/sleeve 123 interface. FIG. 5 is a stator 120 cross section that illustrates the windings that form the coils 122. The stator has epoxy 124 interposed between the metal yoke 121 and the coil 122 and between the coil 122 and the sleeve 123. The sleeve 123 illustrated in FIG. 5 is a plastic sleeve.

One skilled in the art is aware that a variety of epoxy adhesives are suitable for use in a blood pump. US Patent Publication No. 20180280598, which is entitled Thermistor Imbedded [sic] Therapeutic Catheter, describes an intracardiac blood pump that includes an electrically driven motor, a rotor positioned within the blood pump (for example in the cannula), and an electrical line configured to supply current to the motor. In some embodiments the motor is implanted with the rotor. Optionally, the pump is described as powered by an external motor with a drive cable that extends through the catheter and out to a drive unit located external to the patient. US Patent Publication No. 20180280598 is incorporated by reference herein. US Patent Publication describes a blood pump that has a thermistor with a temperature sensitive head. The temperature sensitive head is described as being embedded in epoxy. U.S. Pat. No. 5,089,016 describes an implantable blood pump with a toroidal chamber coated with epoxy (e.g. Stycast Epoxy 1267).

Reliable and consistent blood pump operation is critical to patient care. Therefore, due to the environment in which the pumps are configured to operate, the performance of certain pump components can degrade over time. Therefore, modifications to blood pumps that mitigate such problems continue to be sought.

BRIEF SUMMARY

Described herein is a pump motor for a blood pump and a method for making the pump motor. The pump motor has a rotor portion having proximal and distal ends and a stator portion having proximal and distal ends, wherein the proximal portion of the rotor portion is received into a cavity defined by the stator portion at the distal end of the stator portion. The rotor portion has an impeller, wherein the impeller comprises impeller blades and a drive unit. The impeller blades are positioned at the distal end of the rotor portion and not received into the stator. The drive unit is positioned in a portion of the rotor received into the stator portion. The drive unit is coupled to the impeller blades. The stator portion has a yoke, a coil and a coil holding sleeve. The sleeve defines the cavity into which the proximal portion of the rotor is received.

The yoke, coil and sleeve have interior and exterior surfaces, wherein epoxy is introduced between the yoke and the coil and the coil and the sleeve, thereby substantially embedding the coil in epoxy, wherein at least one of the interior surface of the yoke, the exterior surface of the coil, the interior surface of the coil or the exterior surface of the sleeve are treated with a primer prior to the introduction of epoxy therebetween.

The pump motor is made by assembling a pump motor from a rotor portion with proximal and distal ends and a stator portion having proximal and distal ends. The proximal portion of the rotor portion is received into a cavity defined by the stator portion. The rotor portion has an impeller, wherein the impeller has impeller blades and a drive unit. The impeller blades are positioned at the distal end of the rotor portion and are not received into the stator. The drive unit is positioned in a portion of the rotor received into the stator portion. The drive unit is coupled to the impeller blades. The stator portion has a yoke, a coil and a coil holding sleeve, the sleeve defining the cavity into which the proximal portion of the rotor is received.

The yoke, coil and sleeve have interior and exterior surfaces. According to the method, least one of the interior surface of the yoke, the exterior surface of the coil, the interior surface of the coil or the exterior surface of the sleeve are treated with a primer. After the one or more surfaces are treated, epoxy is introduced between the yoke and the coil and the coil and the sleeve, thereby substantially embedding the coil in epoxy.

BRIEF DESCRIPTION OF DRAWINGS

FIG. 13A illustrates a stator tear down with good adhesion between the yoke and the epoxy;

FIG. 15 illustrates primer effectiveness for reducing leakage current.

DETAILED DESCRIPTION

Blood pumps are deployed in patients that require critical and life-saving care. Consequently, it is important to remediate any aspect of the device that might adversely affect pump operation. Leakage Current (LC) is one such failure mode.

One cause of leakage current is the moisture ingress into the pump stator/rotor assembly. Moisture ingress can occur at the interface between the epoxy and sleeve (such moisture ingress illustrated in FIG. 6A) and between the epoxy and the yoke (such moisture ingress illustrated in FIG. 6B). As noted above, the stator of such blood pumps has a coil 122 that is essentially embedded in epoxy. The epoxy encapsulates the coil and fills the cavity to form the stator body.

Suitable epoxies for assembling the stator described herein are well known to those skilled in the art and not described in detail herein. Examples of suitable epoxies are an amine base two-part epoxy such as Delo-Duopox, which is obtained from DELO Industrial Adhesives and EPO-TEK® 301 from Epoxy Technology, Inc. of Billerica, MA. Suitable epoxies for use in blood pumps are well known to those skilled in the art and are not described in detail herein.

Figure 1:
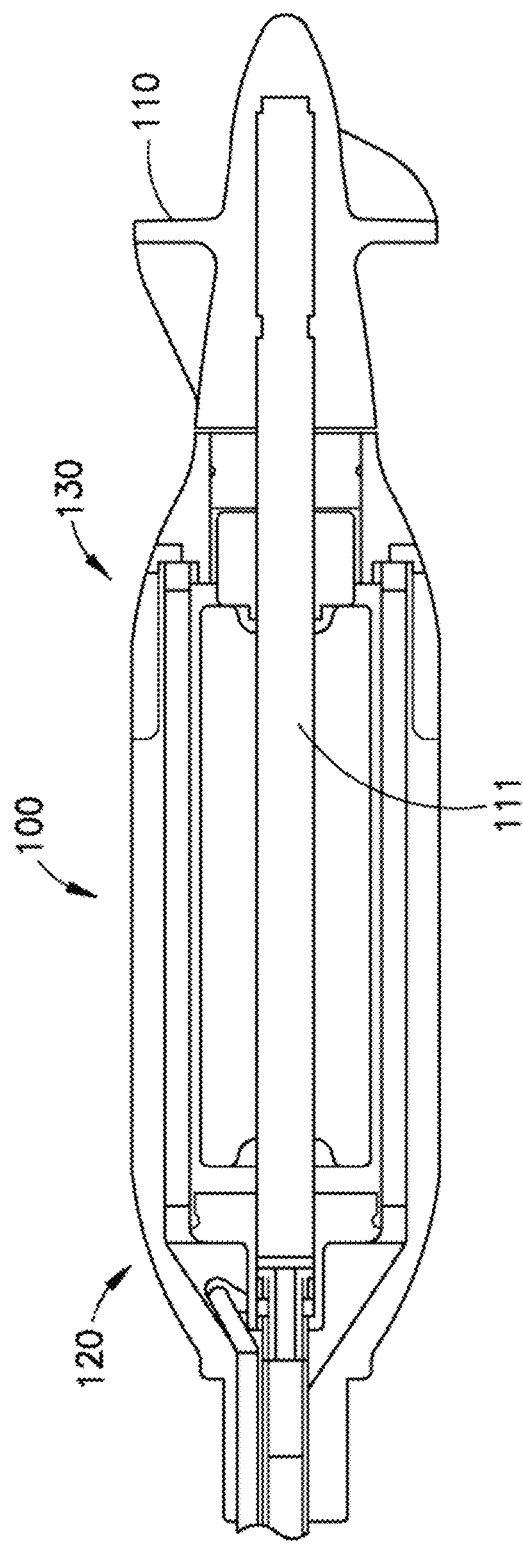
FIG. 1 illustrates a blood pump motor having a stator and a rotor.
Figure 2:
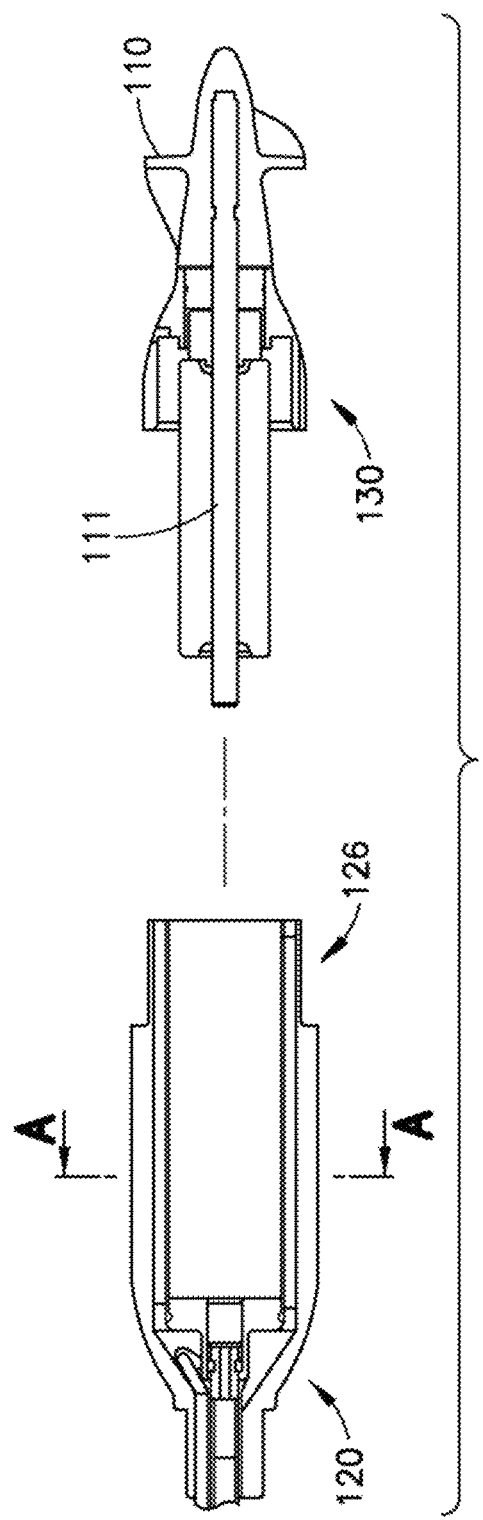
FIG. 2 illustrates an exploded view of the blood pump motor of FIG. 1.
Figure 3:
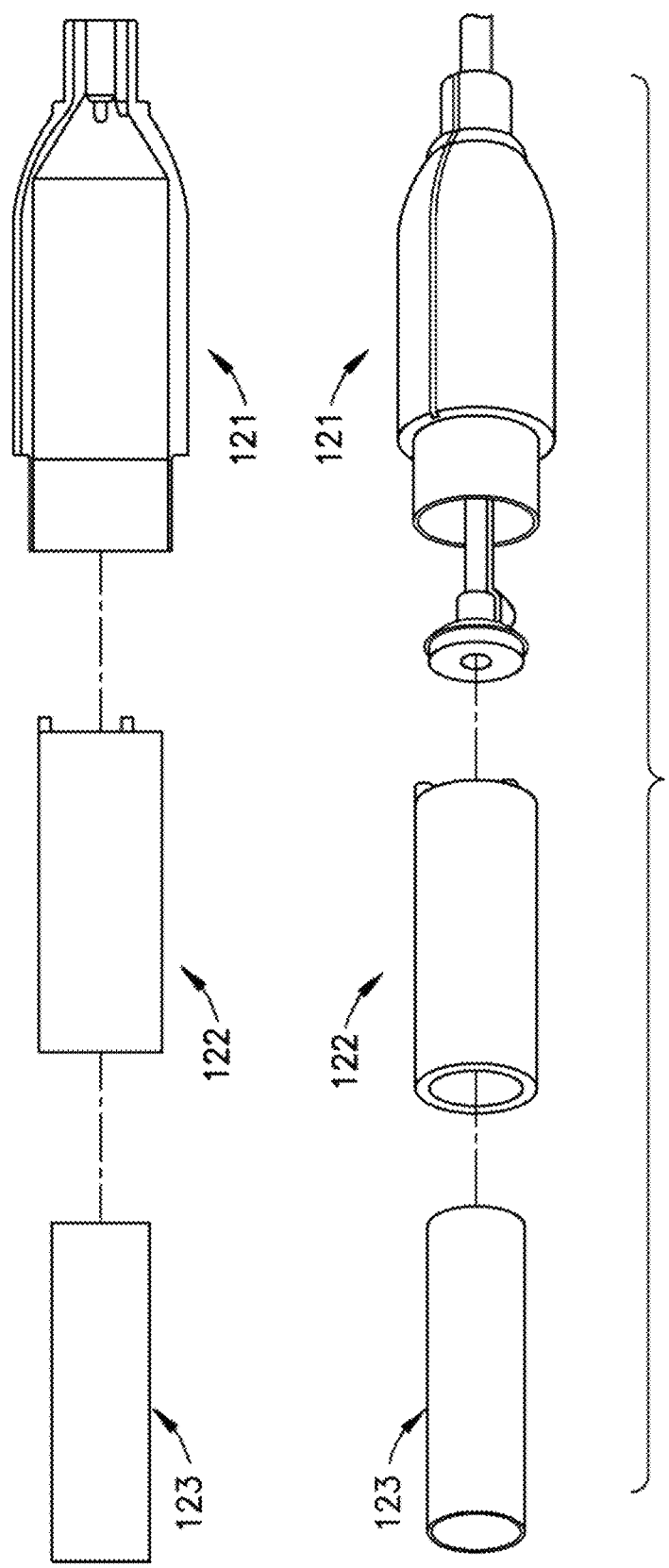
FIG. 3 is an exploded view of the stator of FIG. 2.
Figure 4:
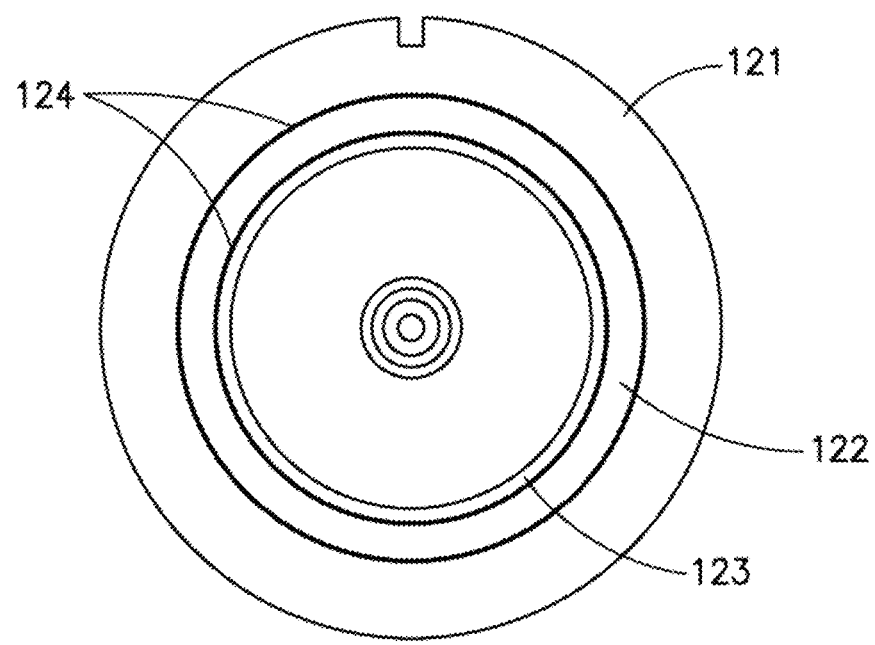
FIG. 4 is a cross section of the stator of FIG. 2 along line A-A.
Figure 5:
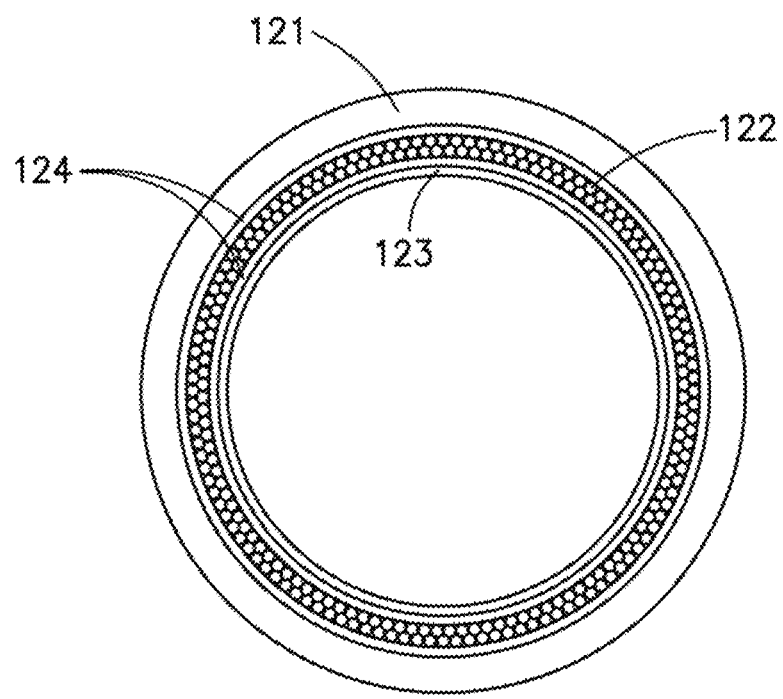
FIG. 5 is another view of the stator cross-section of FIG. 4.
Figure 6:
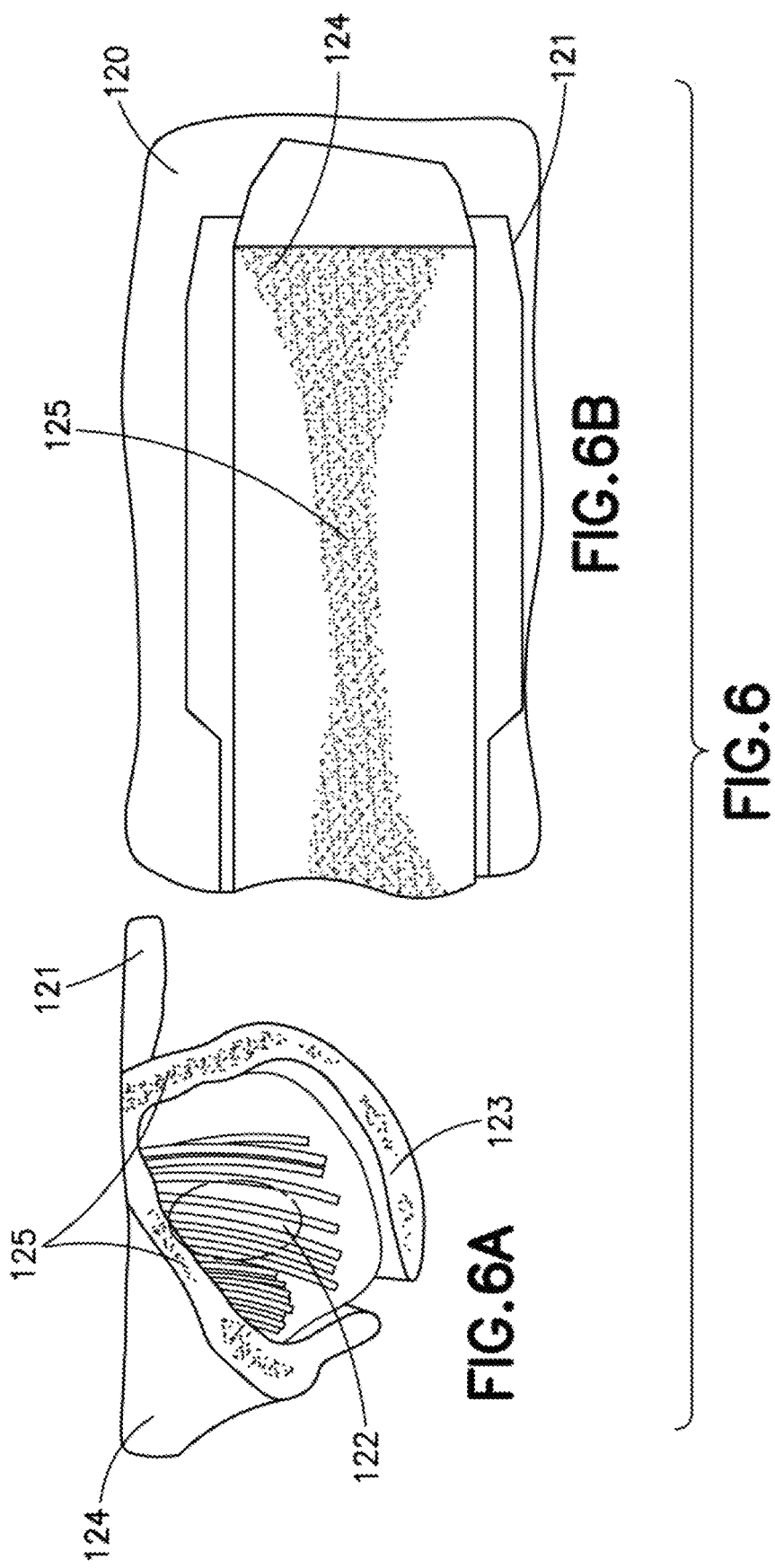
FIGS. 6A-B illustrate the effect of moisture ingress in a blood pump rotor (FIG. 6A) and stator (FIG. 6B)

FIG. 6A illustrates moisture ingression evidence on a coil 122, the moisture ingression from the distal end 126 (FIG. 2) of the stator 120. The moisture is indicated by the shaded areas 125. FIG. 6B illustrates evidence of moisture ingression 125 on the epoxy 124 adjacent the yoke 121, a portion of which is removed to reveal that the epoxy had not adhered well thereto.

Therefore, due to the environment in which the pumps are configured to operate, the performance of certain pump components can degrade over time. Pumps that mitigate such problems are described herein. The method and device described herein increases the bonding strength between the yoke and the epoxy by improving the wettability of the substrate surface (i.e. the surface to which the epoxy is intended to adhere) by the uncured epoxy. The increased bonding strength prevents moisture ingress. Moisture ingress indicates poor adhesion between the sleeve (either ceramic or plastic) and the epoxy. Bonding to ceramic sleeves (e.g. alumina toughened zirconia (ATZ)) in particular is difficult due to the topology of ceramic surfaces.

In the assembly of the blood pump, the epoxy is applied in multiple locations. The epoxy encapsulates the coils to isolate and insulate the coils from the components adjacent to the coils that could otherwise contact the coils. The epoxy also fills the spaces/voids between the sleeve, the coil and the yoke, thereby providing structural strength to the assembled blood pump and avoiding/preventing/mitigating micromovement of the assembled blood that might otherwise occur as the external environment of the pump changes. The epoxy also facilitates the heat transfer from the coils to outside the pump.

However, the gaps between the sleeve, coils and the yoke into which the epoxy is introduced are very small. Such gaps are typically about one micron. As a result, it is important to have a reliably good and consistent surface wettability of the pump component (e.g. coil, sleeve, yoke, etc.) to the uncured epoxy. When the epoxy is injected into the cavities or gaps, a higher wettability surface causes the epoxy to spread evenly and completely fill the small gaps between the pump components. The improved surface wettability for the uncured epoxy results in a higher bonding strength of the epoxy to the adjacent component and excellent encapsulation of components such as the coil. On the contrary, if the substrate (i.e. the component surface) wettability is low or the surface is not otherwise compatible with the uncured epoxy, the uncured epoxy flows away from the substrate surface. As a result of low or poor surface wettability, a low bonding strength between the epoxy and the substrate, or gaps between the substrate and the epoxy, or both, will occur.

The low bonding strength or the gaps between the epoxy and the substrate allow paths to form at the interface between the cured epoxy and the surface of the adjacent pump component through which moisture can travel. Also, gaps function as a heat insulator, which adversely affects the efficiency of heat transfer from the coils to the pump exterior. As a result, the amount of heat dissipated from the coil can be dramatically reduced.

Figure 14:
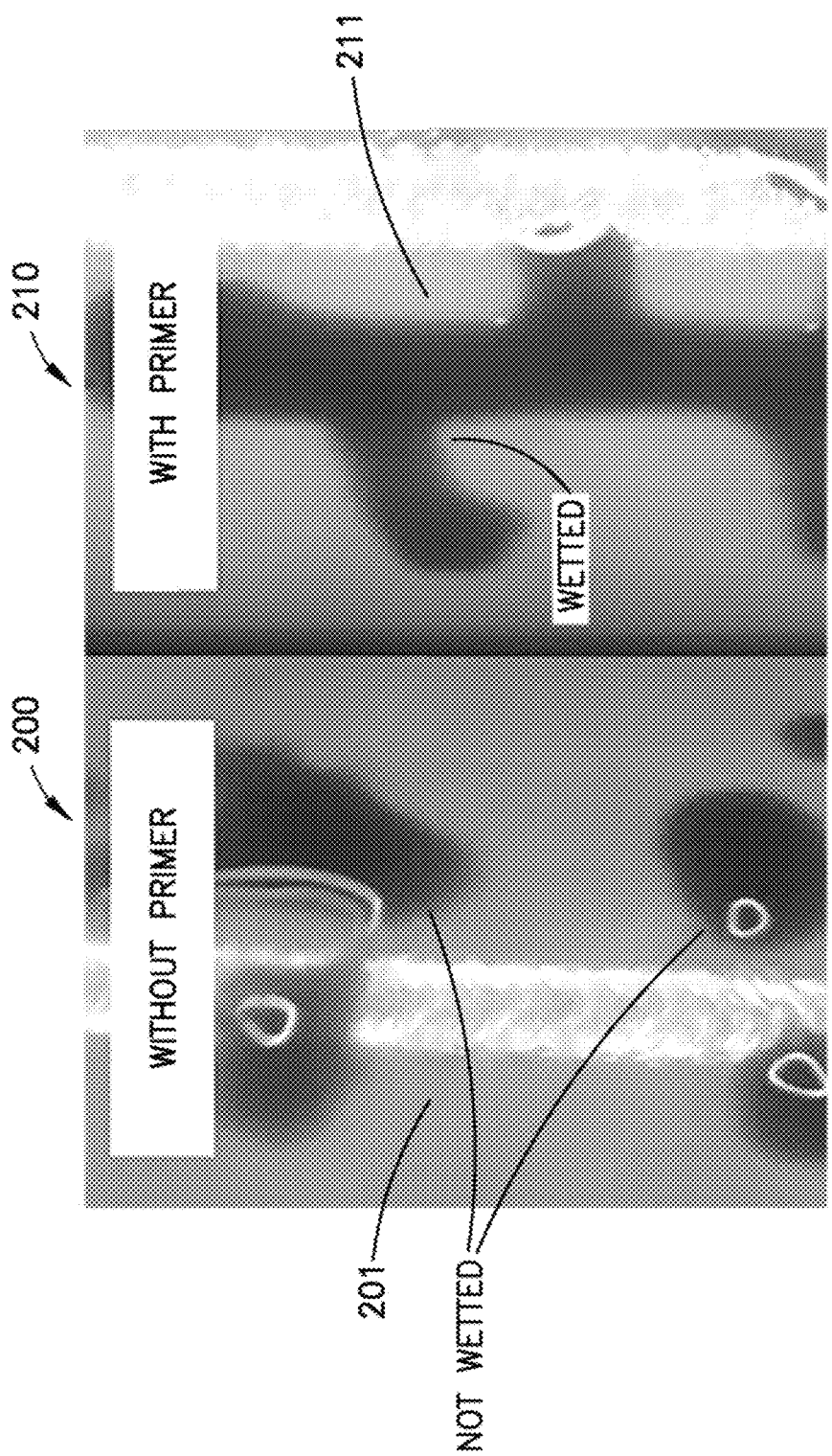
FIG. 14 illustrates the effect of primer on surface wettability.

Disclosed herein is an apparatus and method that describes a simple substrate surface treatment that will improve surface-wettability of the substrate to which the epoxy will adhere, improving both the bonding strength of the epoxy to the substrate and the extent of the bonding between the epoxy and the substrate surface. Referring to FIG. 14, the wettability of a primer-treated ceramic surface 210 (i.e. the sleeve) and a non-treated ceramic surface 200 is illustrated. Referring to surface 200, the isolated shaded regions 201 (i.e., the beaded regions) indicate that the fluid 201 applied to the substrate surface 200 was not compatible with the substrate surface 200. Consequently, the fluid 201 forms on the surface 200 as liquid beads leaving a substantial area of the substrate surface 200 uncovered by the liquid. On the other end, the surface 210 is more substantially covered by the liquid 211, indicating that surface 210 is more compatible with the liquid. The liquid 211 is more uniformly spread around the surface 211 and, as a consequence of the increased substrate surface wetting, there will be increased bonding strength between the substrate surface and the cured epoxy. FIG. 14 illustrates that the primer-treated surface described herein enhances the quality of the bond between the epoxy and the substrate.

The primers described herein not only improve wettability of the substrate to the uncured epoxy, but also modify the substrate surfaces that are otherwise hydrophilic and make those surfaces hydrophobic. The resulting hydrophobic surfaces resist moisture ingress into any remaining gaps between the epoxy and the substrate.

Figure 9:
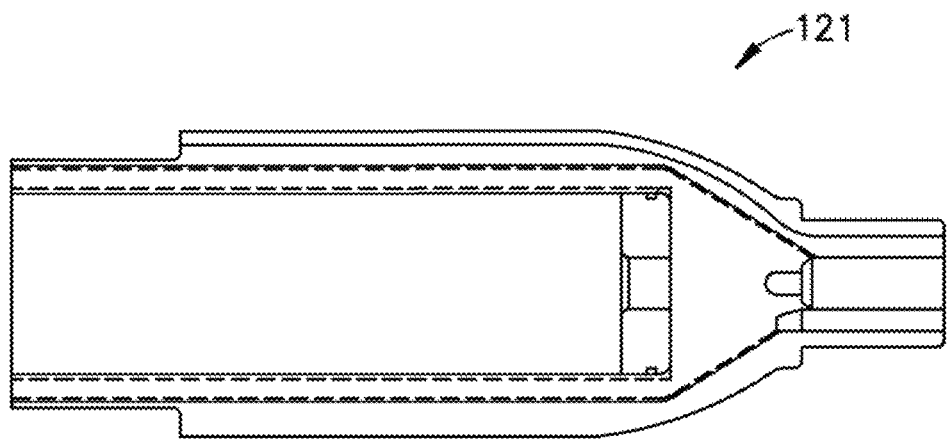
FIG. 9 illustrates a yoke with an interior surface that is surface treated.
Figure 10:
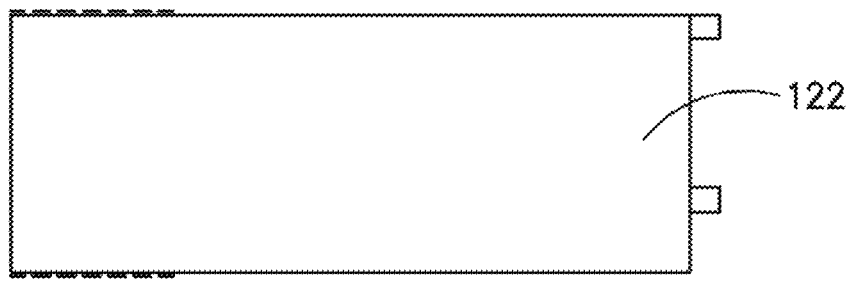
FIG. 10 illustrates a coil with an exterior surface that is surface treated.
Figure 11:
FIG. 11 illustrates a sleeve with an exterior surface that is surface treated
Figure 13:
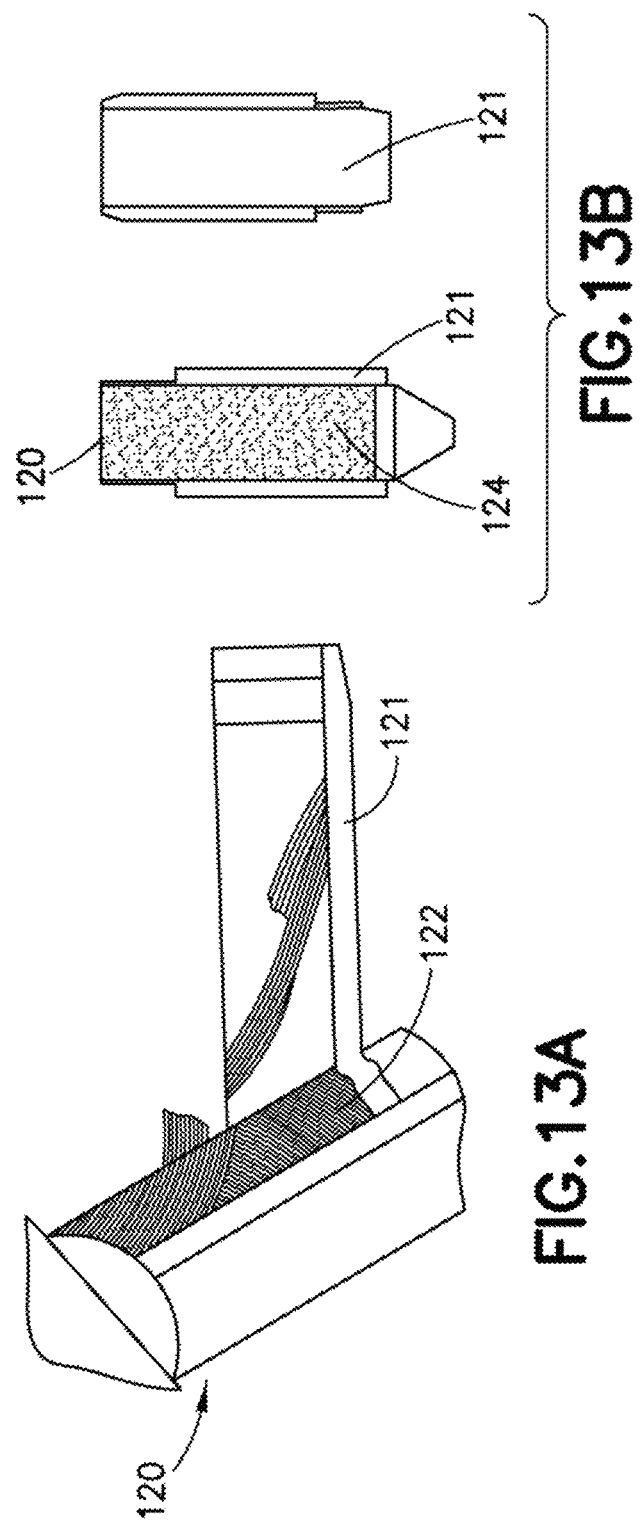
FIG. 13 B illustrates a stator tear down with poor adhesion between the yoke and the epoxy.

The method and device described herein deploys a primer onto the epoxy (or the surface to which the epoxy will adhere). The primer improves adhesion of the bonding surface to the epoxy. The positive effect of applying primer to enhance the adhesion to a substrate material is illustrated in FIG. 13A. FIG. 13A illustrates a stator 120 in which a portion of the yoke 121 is separated from the stator 120. The stator 120 in FIG. 13A had epoxy 124 treated with a silane solution. Silane solutions are known primers that function at the interface between the uncured epoxy and act as an adhesion promoter. The silane primer is chosen by matching its organic functionality to the polymer to optimize bonding. The selection of a silane primer that will render the substrate surface hydrophobic and enhance surface wettability/bonding with the epoxy is described in *A Guide to Silane Solutions* @2009 Dow Corning Corporation, which is incorporated by reference herein. Silane coupling agents contain two types of reactivity, inorganic and organic, in the same molecule. Silane have the general chemical formula $(RO)_3SiCH_2CH_2CH_2$—X wherein RO is a hydrolysable group such as methoxy, ethoxy, or acetoxy and X in an organo-functional group such as amino, methacryloxy, epoxy, etc. One skilled in the art can select a suitable silane primer for use with the present invention. The alkoxy groups hydrolyze and the resulting hydroxyl groups bond to the hydroxyl groups on the inorganic substrate surfaces (e.g., the metal, metal oxide and ceramic surfaces described herein. The epoxy adheres strongly to the primed surface of the yoke 121 such that the epoxy and even a portion of the coil 122 is torn away with the portion of the yoke 121 separated from the stator 120. The surface treatment is performed prior to the stator being injection molded. Basically, here is a brief flow: 1). the coil is attached to the sleeve; 2). wires and cables are soldered to a printed circuit board (PCB) which is then adhered to the ceramic sleeve; 3). the yoke inner diameter (ID) is treated with primer (FIG. 9); 4). the sleeve/coil outer diameter (OD) is then treated with primer (FIGS. 10 and 11); 5). the yoke is installed over the sleeve/coil subassembly; and 6). epoxy is injected into the assembly.

Figure 12:
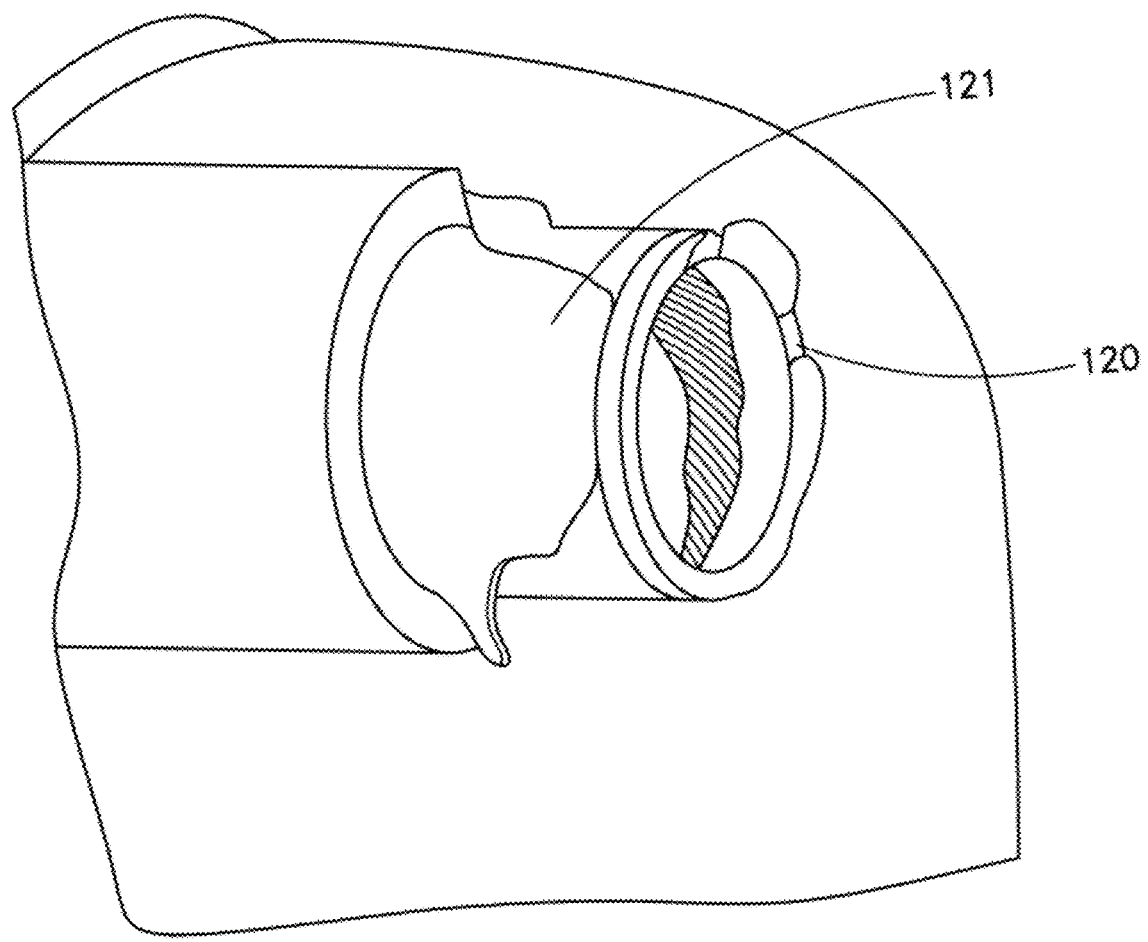
FIG. 12 is an image of a stator with a portion of the yoke removed to reveal moisture ingress evidence into the epoxy underlying the yoke.

The stator 120 in FIGS. 12 and 13B did not have primer applied to the interior surface of the yoke 121. This is apparent since the portion of the yoke 121 that is separated from the stator 120 has no epoxy 124 thereon. This illustrates that there was little to no bonding of the epoxy 124 to the yoke 121 in the stator 120 illustrated in FIG. 13B. FIG. 6B also illustrates a stator 120 in which the epoxy 124 did not adhere to the portion of the yoke 121 removed from the stator. As stated above, the shaded epoxy region 124 indicates moisture ingress, demonstrating that, due to the poor adhesion between the epoxy 124 and the yoke 121, moisture was able to migrate into the interface between the yoke 121 and the epoxy 124. Contrast the stator in FIG. 13B with that in FIG. 13A, where the bonding surface was treated as described herein. The yoke 121 was significantly damaged when a portion of the yoke 121 was separated from the stator 120.

The primer also improves the bond between the sleeve 123 and the epoxy 124. Just as the epoxy 124 remains adhered to the portion of the yoke 121 separated from the stator 120, at least a portion of the epoxy will remain adhered to the sleeve 123 during a tear down process in which the sleeve (or a portion thereof) is separated from the stator 120.

Figure 7:
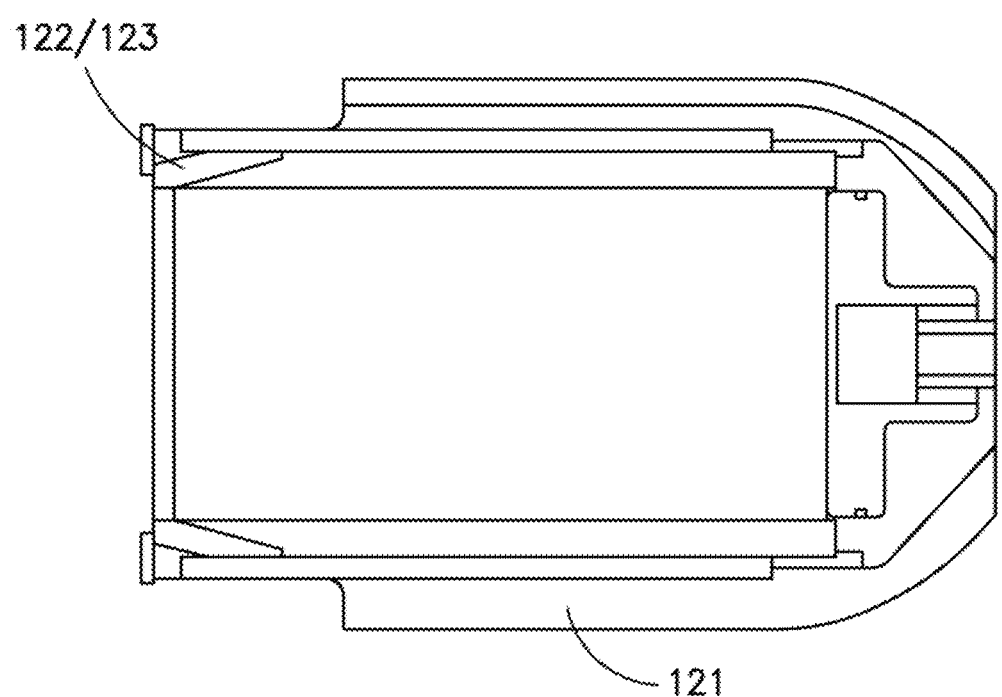
FIG. 7 illustrates a blood pump motor according to one embodiment of the present invention.
Figure 8A:
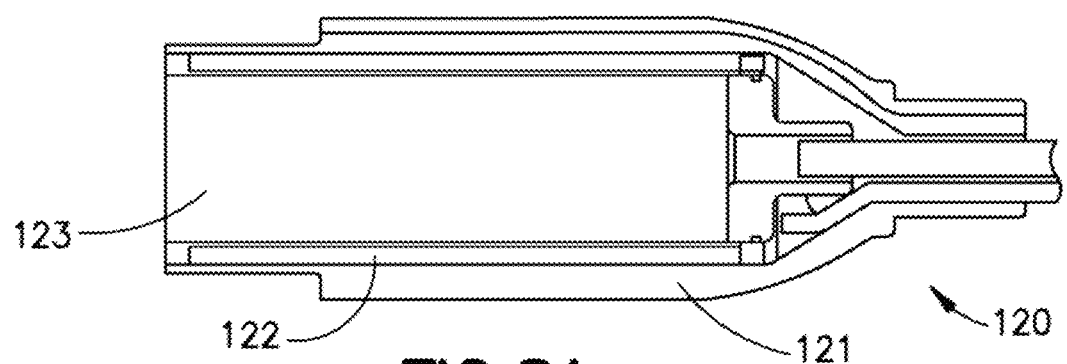
FIGS. 8A-B illustrate the stator with coated surfaces.
Figure 8B:
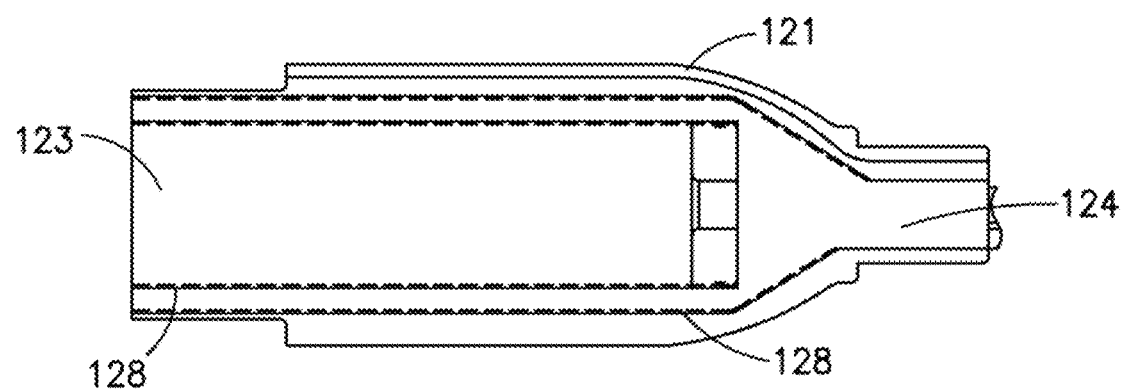

Described herein is a motor for a blood pump in which one or more operating surfaces of the blood pump stator are surface treated to mitigate the problems with moisture that can lead to an increase in leakage current of the motor. FIG. 7 highlights the interface 129 between the yoke 121 and the coil/sleeve 122/123. Referring to FIG. 8A, the stator 120 has a silane treated surface on the interior of the yoke 121, the exterior of the coil 122 and exterior of the sleeve 123. The silane treated surface is 128 in FIG. 8B. In the cross section of FIG. 8B the coil is not visible because it is embedded in the epoxy 124.

In one embodiment a silane primer is provided to improve the bonding between the epoxy and the yoke and or the sleeve. Application of silane primer eliminated the leakage current by improving the adhesion between ceramic sleeve and the epoxy (e.g., EPO-TEK® 301 (ES2019-181 rA).

FIG. 15 illustrates that pumps in which the primer was applied to the surface of at least some of the pump components prior to the introduction of epoxy had consistently lower leakage current. Pumps that were assembled without the application of the primer prior to epoxy injection had a range of leakage current results. Therefore, the application of the primer to the surface of the pump components provides the assembled pumps with reliable and acceptable performance regarding leakage current.

As noted above, wetting of the bonding surfaces as well as chemical bond formation with the bonding surface provides better adhesion between two different surfaces (e.g., the epoxy and the yoke surface or the sleeve surface.

As noted above, the primers described herein are silane-based primers. Such primers improve the wetting of epoxies such as EPO-TEK® 301 on the surface of the ceramic sleeve or the metal yoke for better adhesion. As noted above, the silane forms a chemical bond with the substrate surface and with the epoxy that improves the adhesion strength between the epoxy and the substrate (e.g. the metal yoke/ceramic sleeve of the pump). Silane based primers that act as coupling agent between the relevant pump component and the adjacent epoxy that are both hydrophobic and organophilic are contemplated as suitable herein.

In this specification, the word "comprising" is to be understood in its "open" sense, that is, in the sense of "including", and thus not limited to its "closed" sense, that is the sense of "consisting only of". A corresponding meaning is to be attributed to the corresponding words "comprise", "comprised" and "comprises" where they appear.

While particular embodiments of this technology have been described, it will be evident to those skilled in the art that the present technology may be embodied in other specific forms without departing from the essential characteristics thereof. The present embodiments and examples are therefore to be considered in all respects as illustrative and not restrictive. It will further be understood that any reference herein to subject matter known in the field does not, unless the contrary indication appears, constitute an admission that such subject matter is commonly known by those skilled in the art to which the present technology relates.

We claim:

1. A method of reducing moisture ingress in a blood pump motor, the method comprising:
assembling the blood pump motor comprising a rotor portion having a proximal portion and a distal portion and a stator portion having a proximal portion and a distal portion;
receiving the proximal portion of the rotor portion into a cavity defined by the stator portion,
wherein the rotor portion comprises an impeller, wherein the impeller comprises impeller blades and a drive unit, the impeller blades positioned at the distal portion of the rotor portion and not received into the stator portion and the drive unit positioned in the proximal portion of the rotor portion received into the stator portion, wherein the drive unit is coupled to the impeller blades,
wherein the stator portion comprises a yoke, a coil and a coil holding sleeve, the yoke defining a cavity into which the coil holding sleeve is received, the coil disposed around and held on an exterior of the coil holding sleeve, the coil holding sleeve defining the cavity into which the proximal portion of the rotor portion is received,
wherein the yoke, the coil and the coil holding sleeve each have an interior surface and an exterior surface;
treating the exterior surface of the coil holding sleeve with a primer;
treating the interior surface of the yoke with the primer; and
injecting an epoxy between the yoke and the coil and the coil and the coil holding sleeve, thereby substantially embedding the coil in epoxy such that the primer is interposed between (i) the exterior surface of the coil holding sleeve and the epoxy and (ii) the interior surface of the yoke and the epoxy, and reduces moisture ingress in the blood pump motor.

2. The method of claim 1, wherein a gap between the yoke and the coil and a gap between the coil and the coil holding sleeve is about 1 micron each.

3. The method of claim 2, wherein the epoxy is injected in the gap between the yoke and the coil and the gap between the coil and the coil holding sleeve.

4. The method of claim 3, wherein the epoxy fills the gap between the yoke and the coil and the gap between the coil and the coil holding sleeve.

5. The method of claim 3, wherein the epoxy completely fills the gap between the yoke and the coil and the gap between the coil and the coil holding sleeve.

6. The method of claim 2, wherein the primer modifies the exterior surface of the coil holding sleeve and the interior surface of the yoke to be hydrophobic, thereby resisting moisture ingress in the gap between the yoke and the coil and the gap between the coil and the coil holding sleeve.

7. The method of claim 1, wherein the coil holding sleeve comprises ceramic.

8. The method of claim 1, further comprising treating at least one of the exterior surface of the coil or the interior surface of the coil with the primer.

9. The method of claim 1, further comprising injection molding the stator portion.

10. The method of claim 9, wherein the injection molding the stator portion is performed after treating the exterior surface of the coil holding sleeve and the interior surface of the yoke with the primer.

11. The method of claim 1, wherein the primer is a silane solution.

12. The method of claim 11, wherein the silane solution has the general chemical formula $(RO)_3SiCH_2CH_2CH_2-X$ wherein RO is a hydrolysable group.

13. The method of claim 12, wherein the hydrolysable group is selected from the group consisting of methoxy, ethoxy, or acetoxy.

14. The method of claim 13, wherein X is an organofunctional group.

* * * * *